United States Patent
Mullins et al.

(10) Patent No.: US 6,768,105 B2
(45) Date of Patent: Jul. 27, 2004

(54) METHODS AND APPARATUS FOR DOWNHOLE FLUIDS ANALYSIS

(75) Inventors: Oliver C. Mullins, Ridgefield, CT (US); Toru Terabayashi, Sagamihara (JP); Kazuyoshi Kegasawa, Sagamihara (JP); Ikko Okuda, Hachioji (JP)

(73) Assignee: Schlumberger Technology Corporation, Sugar Land, TX (US)

( * ) Notice: Subject to any disclaimer, the term of this patent is extended or adjusted under 35 U.S.C. 154(b) by 162 days.

(21) Appl. No.: 10/238,792

(22) Filed: Sep. 10, 2002

(65) Prior Publication Data

US 2003/0062472 A1 Apr. 3, 2003

Related U.S. Application Data

(63) Continuation of application No. 09/686,646, filed on Oct. 10, 2000, now Pat. No. 6,476,384.

(51) Int. Cl.[7] .................................................. G01V 5/08
(52) U.S. Cl. .................................................. 250/269.1
(58) Field of Search ....................................... 250/269.1

(56) References Cited

U.S. PATENT DOCUMENTS

| | | |
|---|---|---|
| 5,166,747 A | 11/1992 | Schroeder et al. |
| 5,473,939 A | 12/1995 | Leder et al. |
| 5,635,631 A | 6/1997 | Yesudas et al. |
| 5,741,962 A | 4/1998 | Birchak et al. |
| 5,934,374 A | 8/1999 | Hrametz et al. |
| 6,218,662 B1 | 4/2001 | Tchakarov et al. |
| 6,350,986 B1 | 2/2002 | Mullins et al. |
| 6,388,251 B1 | 5/2002 | Papanyan |
| 6,437,326 B1 | 8/2002 | Yamate et al. |
| 6,467,340 B1 | 10/2002 | Gallagher et al. |
| 6,474,152 B1 | 11/2002 | Mullins et al. |
| 6,476,384 B1 | 11/2002 | Mullins et al. |
| 6,507,401 B1 * | 1/2003 | Turner et al. ............... 356/436 |

FOREIGN PATENT DOCUMENTS

| | | |
|---|---|---|
| WO | WO 9714951 A1 | 4/1997 |
| WO | WO 02/043620 A1 | 6/2002 |
| WO | WO 02/084334 A1 | 10/2002 |

\* cited by examiner

*Primary Examiner*—Constantine Hannaher
(74) *Attorney, Agent, or Firm*—Robin Nava; Bill Batzer; Brigitte Jeffery

(57) ABSTRACT

A method of determining GOR comprising subjecting a fluid to spectroscopic analysis at a first wavelength sensitive to gas and a second wavelength sensitive to oil, determining a response matrix for the contribution of gas at the first and second wavelengths and the contribution of oil at the first and second wavelengths, determining a signal response vector and the two wavelengths, calculating a mass fraction vector from the response matrix and the signal response vector and using the mass fraction vector to determine GOR.

22 Claims, 12 Drawing Sheets

F I G. 14
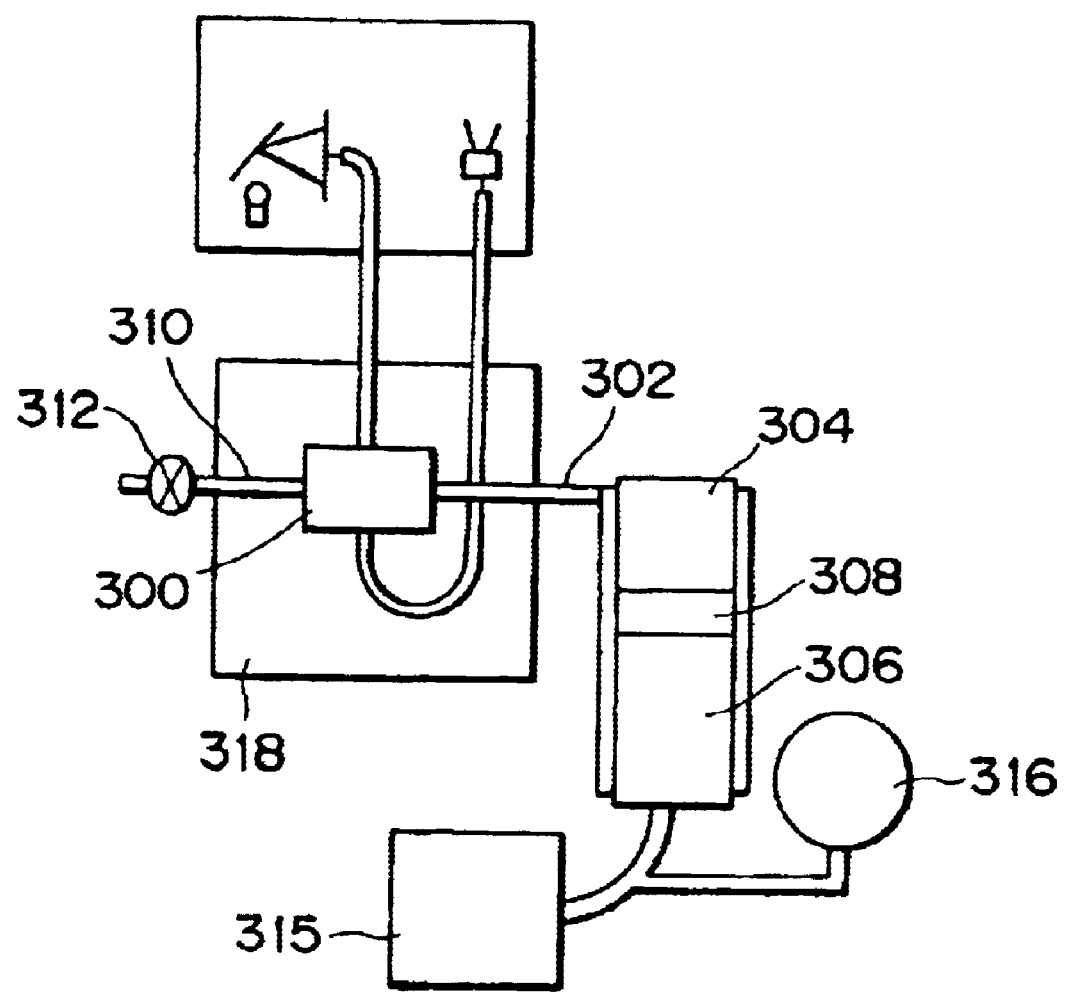

F I G. 15
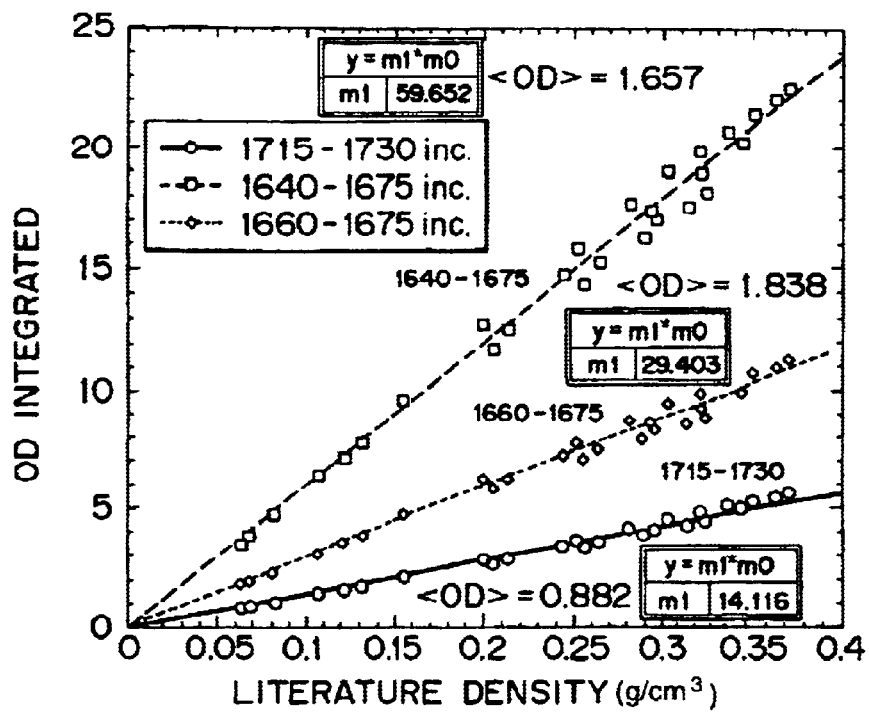
F I G. 16
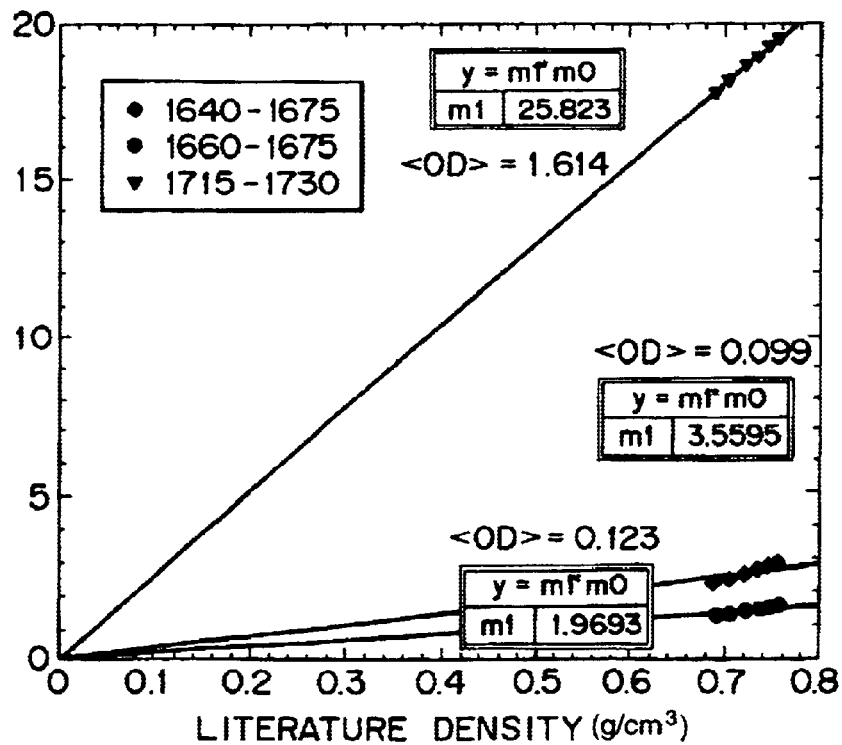

METHODS AND APPARATUS FOR DOWNHOLE FLUIDS ANALYSIS

This application is a continuation of U.S. application Ser. No. 09/686,646, filed Oct. 10, 2000, now U.S. Pat. No. 6,476,384.

FIELD OF THE INVENTION

The present invention relates to the field of downhole fluid analysis applicable to formation evaluation and testing in the exploration and development of hydrocarbon-producing wells such as oil or gas wells. In particular, the invention provides methods and apparatus suitable for performing downhole analysis on fluids produced in such wells using optical techniques.

BACKGROUND AND PRIOR ART

In order to evaluate the nature of underground formations surrounding a borehole, it is often desirable to obtain samples of formation fluids from various specific locations in a borehole. Tools have been developed which allow several samples to be taken from the formation in a single logging run. Examples of such tools can be found in U.S. Pat. No. 3,780,575 and U.S. Pat. No. 3,859,851.

The RFT and MDT tools of Schlumberger represent two specific versions of sampling tools. In particular, the MDT tool includes a fluid analysis module to allow analysis of the fluids sampled by the tool. FIG. 1 shows a schematic diagram of such a tool and includes a borehole tool 10 for testing earth formations and analysing the composition of fluids from the formation is shown in FIG. 1. The tool 10 is suspended in the borehole 12 from the lower end of a logging cable 15 that is connected in a conventional fashion to a surface system 18 incorporating appropriate electronics and processing systems for control of the tool. The tool 10 includes an elongated body 19 which encloses the downhole portion of the tool control system 16. The body 19 also carries a selectively extendible fluid admitting assembly 20 (for example as shown in the '575 and '851 patents referenced above, and as described in U.S. Pat. No. 4,860,581, incorporated herein by reference) and a selectively extendible anchoring member 21 which are respectively arranged on opposite sides of the body 19. The fluid admitting assembly 20 is equipped for selectively sealing off or isolating portions of the wall of the borehole 12 such that pressure or fluid communication with the adjacent earth formation is established. A fluid analysis module 25 is also included within the tool body 19, through which the obtained fluid flows. The fluid can then be expelled through a port (not shown) back into the borehole, or can be sent to one or more sample chambers 22, 23 for recovery at the surface. Control of the fluid admitting assembly, the fluid analysis section and the flow path to the sample chambers is maintained by the electrical control systems 16, 18.

The OFA, which is a fluid analysis module 25 as found in the MDT mentioned above, determines the identity of the fluids in the MDT flow stream and quantifies the oil and water content. In particular, U.S. Pat. No. 4,994,671 (incorporated herein by reference) describes a borehole apparatus which includes a testing chamber, means for directing a sample of fluid into the chamber, a light source preferably emitting near infrared rays and visible light, a spectral detector, a data base means, and a processing means. Fluids drawn from the formation into the testing chamber are analysed by directing the light at the fluids, detecting the spectrum of the transmitted and/or backscattered light, and processing the information accordingly (and preferably based on the information in the data base relating to different spectra), in order to quantify the amount of water and oil in the fluid. Thus, the formation oil can be properly analysed and quantified by type.

U.S. Pat. No. 5,167,149, and U.S. Pat. No. 5,201,220 (both incorporated by reference herein) describe apparatus for estimating the quantity of gas present in a flow stream. A prism is attached to a window in a flow stream and light is directed through the prism to the window and light reflected from the window/flow interface at certain specific angles is detected to indicate the presence of gas in the flow.

As set forth in U.S. Pat. No. 5,266,800 (incorporated herein by reference), by monitoring optical absorption spectrum of the fluid samples obtained over time, a determination can be made as to when a formation oil is being obtained as opposed to a mud filtrate. Further, as set forth in U.S. Pat. No. 5,331,156 to Hines, by making optical density (OD) measurements of the fluid stream at certain predetermined energies, oil and water fractions of a two-phase fluid stream may be quantified.

In situ gas quantification is described in U.S. Pat. No. 5,167,149, and U.S. Pat. No. 5,201,220 (both incorporated by reference herein), where a rough estimate of the quantity of gas present in the flow stream can be obtained by providing a gas detection module having a detector array which detects reflected light rays having certain angles of incidence.

Gas:Oil ratio (GOR) is an important property of fluids obtained from hydrocarbon wells and which is normally only measured at the surface. U.S. Pat. No. 5,939,717 (incorporated herein by reference) describes methods for determining GOR which include providing an OFA module which subjects formation fluids to NIR illumination and which provides a spectral measurement of peaks at about 6,000 $cm^{-1}$ and about 5,800 $cm^-$. The methods include calculating a ratio of the amplitudes of the absorption peaks to determine GOR. Alternatively, the methods of calculating the ratio include referring to a database of spectra of hydrocarbons found in formation fluid and adjusting the amplitudes of the methane and oil peaks to account for the influences of other hydrocarbons on the spectrum of the formation fluid.

While GOR is in itself a useful measurement, the development of the measured GOR over time as fluids flow from the formation into the OFA flow line can be used to determine the degree of contamination of the formation fluids by oil-based mud filtrate or the like. Examples of this approach are found in U.S. Ser. No. 09/255,999, now U.S. Pat. No. 6,274,865 and U.S. Ser. No. 09/300,190, now U.S. Pat. No. 6,350,986 (both incorporated herein by reference).

The present invention seeks to provide improved methods for estimating GOR and associated measurements, methods for interpreting such measurements, and apparatus suitable for making such measurements.

SUMMARY OF THE INVENTION

A first aspect of the present invention provides a method of determining GOR comprising subjecting a fluid to spectroscopic analysis at a first wavelength sensitive to gas and a second wavelength sensitive to oil, determining a response matrix for the contribution of gas at the first and second wavelengths and the contribution of oil at the first and second wavelengths, determining a signal response vector and the two wavelengths, calculating a mass fraction vector from the response matrix and the signal response vector and using the mass fraction vector to determine GOR.

A second aspect of the invention provides apparatus for determining GOR which includes a spectroscopy module operating at least at a first wavelength sensitive to gas and a second wavelength sensitive to oil, means being provided to determine GOR from a mass fraction vector derived from a response matrix and a signal response vector.

A third aspect of the invention provides an method of compensating for temperature effects in spectroscopic measurements on formation fluids, comprising determining temperature dependency curves for source and measurement data, and analysing the fluid based on the measured response and the temperature dependency curves.

A fourth aspect of the invention provides a method for detecting gas in a flow line, comprising subjecting the fluids to spectroscopic measurements in the flow line at least at a wavelength sensitive to the presence of methane, and using the measured response to indicate the presence of gas.

A fifth aspect of the invention provides a method of detecting contaminants in the fluid in a flow line, comprising subjecting the fluids to spectroscopic measurements in the flow line at least at a wavelength sensitive to the presence of methane, and using the measured response to indicate the presence of contaminants.

A sixth aspect of the invention provides apparatus for analysing fluids downhole, comprising two spectroscopic analysis modules connected in series to a flow line, correlation of the outputs of the modules being used to calculate the flow rate of fluid in the flow line.

BRIEF DESCRIPTION OF THE DRAWINGS

FIG. 14 shows an experimental setup for determining GOR;

FIG. 15 shows a plot of integrated average spectrometer OD values for various spectral windows as a function of methane mass density;

FIG. 16 shows a plot of integrated average spectrometer OD values for various spectral windows as a function of n-heptane mass density;

DESCRIPTION OF THE PREFERRED EMBODIMENT

Figure 1:
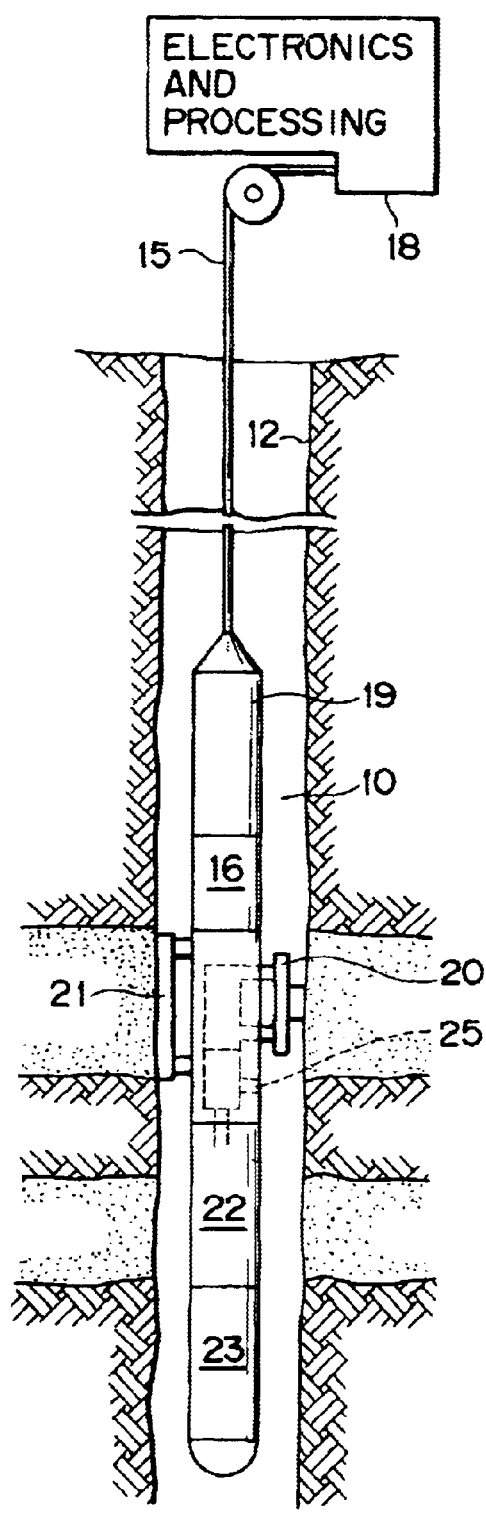
FIG. 1 shows a prior art tool including a fluid analysis module.

The present invention finds its application in tools such as the MDT which is described above in relation to FIG. 1 and in U.S. Pat. No. 4,860,581. Aspects of the MDT tool that are not considered relevant to the present invention nor contributing to its function will not be described below.

In particular, the present invention finds its application in an OFA module of the MDT tool as described above and in U.S. Pat. No. 4,994,671. As with the previous embodiment, a fluid analysis module incorporating the present invention includes a gas detector cell which operates generally as described in U.S. Pat. No. 5,167,149 and U.S. Pat. No. 5,201,220, and a spectroscopy module which operated generally as described in the '671 patent referenced above. The construction and operation of the gas detector cell and spectroscopy module in accordance with the invention will be described in more detail below.

Figure 2:
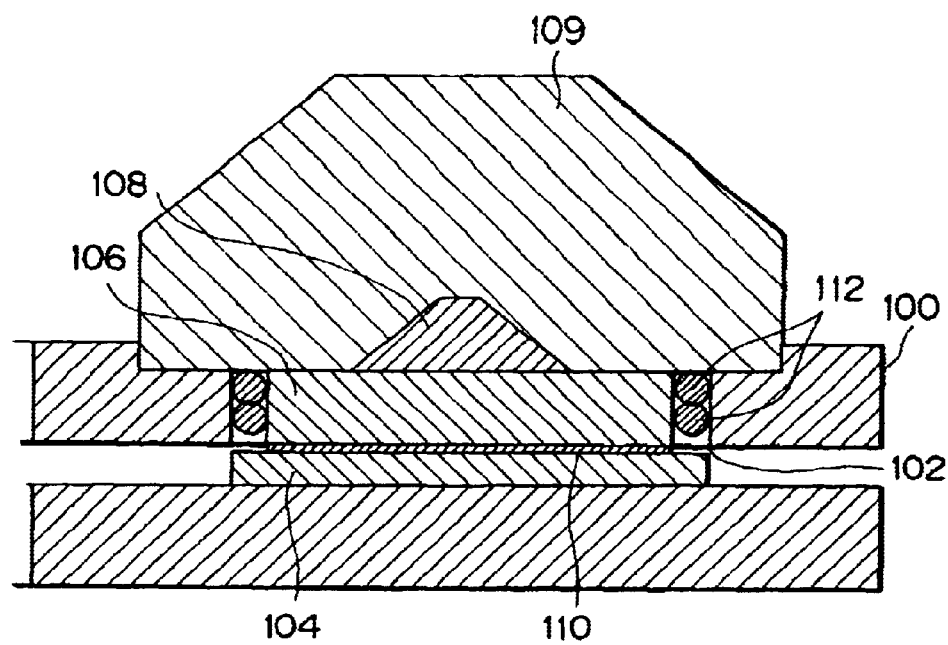
FIG. 2 shows a gas detector cell for use in a tool according to the invention.

The structure of the gas detector cell is shown in more detail in FIG. 2. The cell is formed in a flow line 100 of the MDT which receives fluids from the formation. An opening 102 is provided in the flow line 100 to receive a window, prism and flange structure. A flow channel 104 is provided in the flow line 100 and a sapphire window 106 is mounted in the opening 102 over the channel 104. A sapphire prism 108 is fixed so as to be in optical contact with the surface of the window 106 on the opposite side from the flow channel 104. The window 106 and prism 108 are secured in the opening 102 by means of a stainless steel flange 109 which is screwed onto the flow line 100 and holds the window 106 in place against the pressure of fluids in the flow line 100. Effective sealing is ensured by the use of a fluoropolymer resin (TEFLON) window support 110 between the window 106 and the flow channel 104, and by the use of o-rings 112 around the window 106 in the opening 102. The flange is also provided with optical connectors (not shown in FIG. 2) which optically connect to the upper surface of the prism 108. The upper and lower surfaces of the window 106 and prism 108 are polished to optical quality, the side surfaces of the window 106 are polished to assist sealing.

Figure 3:
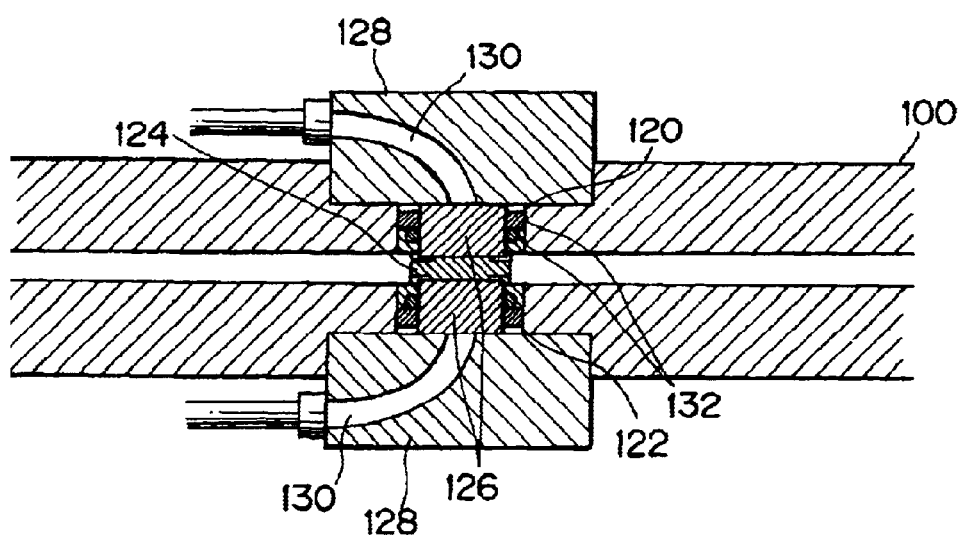
FIG. 3 shows a spectroscopy cell for use in a tool according to the invention.
Figure 4:
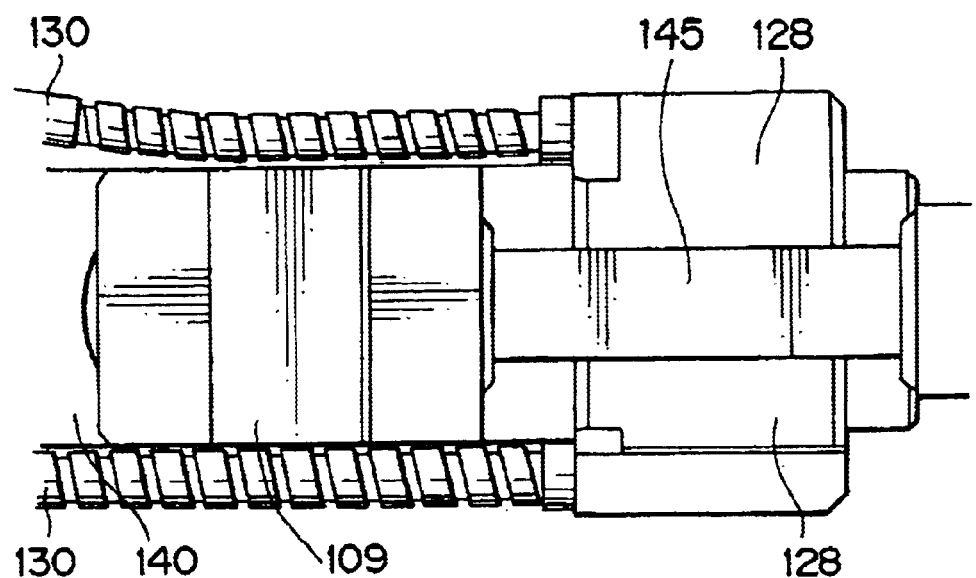
FIG. 4 shows a top view of the gas and spectroscopy cells for use in an embodiment of the invention.
Figure 5:
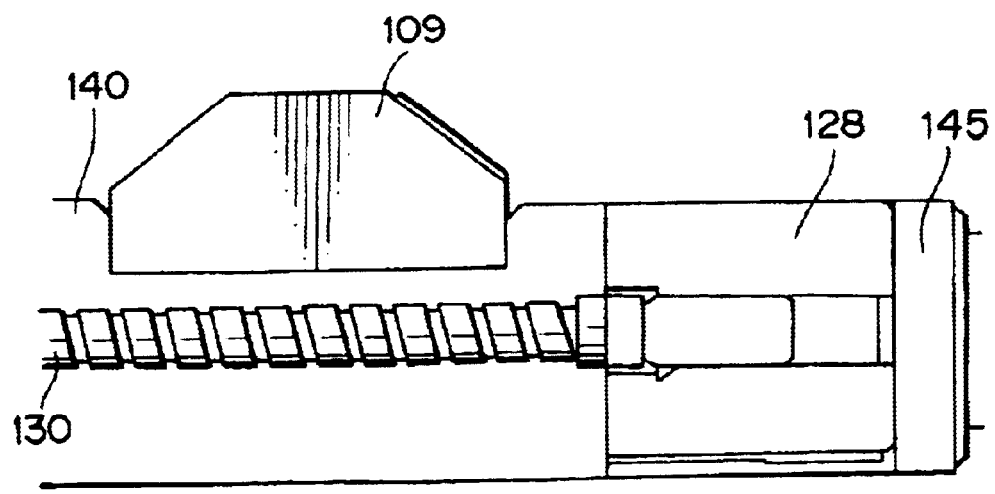
FIG. 5 shows a side view of the gas and spectroscopy cells for use in an embodiment of the invention.
Figure 6:
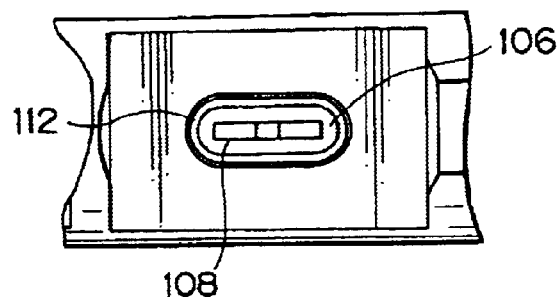
FIG. 6 shows detail of the gas cell window and prism.
Figure 7:
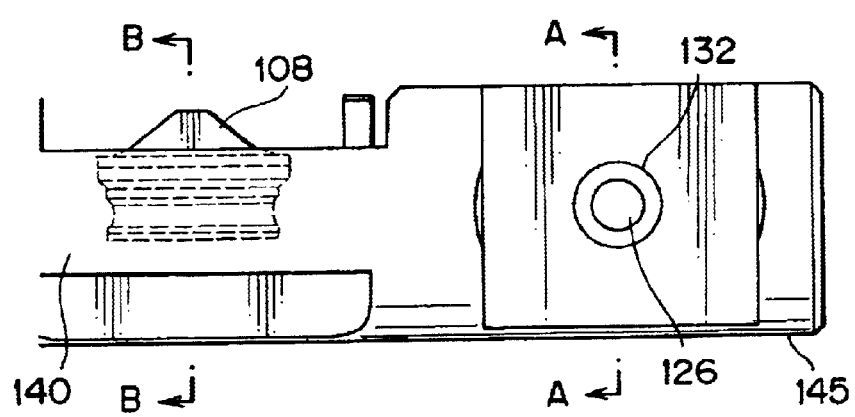
FIG. 7 shows a side view of the gas and spectroscopy cells with parts omitted for clarity.
Figure 8:
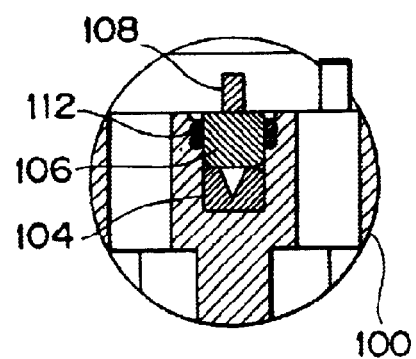
FIG. 8 shows a gas cell cross section on line BB of FIG. 7.
Figure 9:
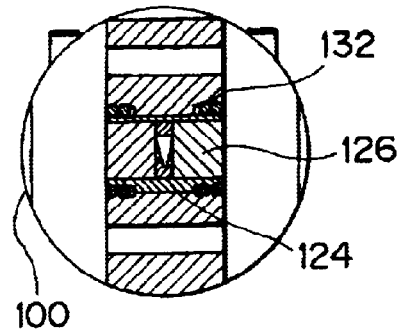
FIG. 9 shows a spectrometer cell cross section on line AA of FIG. 7.

The spectroscopy cell is shown in general detail in FIG. 3. The cell is located in the same flow line 100 as the gas detector cell described above. In this case opposed openings 120, 122 are provided in the flow line 100, each of which receive input and output window and flange structures respectively. Structurally, the input and output sides of the cell are the same so only the input side will be described in detail. A monel flow channel 124 is located in the flow line 100 between the openings 120, 122 and defines window-locating seats. Sapphire windows 126 are located in the seats facing each other across the flow channel 124. The windows 126 are secured in place by stainless steel flanges 128 which are provided with optical connectors to connect the outer faces of the windows 126 with fibre bundles 130. The flanges are screwed to each other so as to seal the windows into the seats. Sealing is assisted by the use of back up rings and o-rings 132. Inner and outer faces of the windows 126 are polished to optical quality, side faces are polished to assist sealing.

The gas detector cell 140 and spectroscopy cell 145 are conveniently provided in a single structure in the flow line which is shown in more detail in FIGS. 4 to 9 with some parts omitted for clarity.

Figure 10:
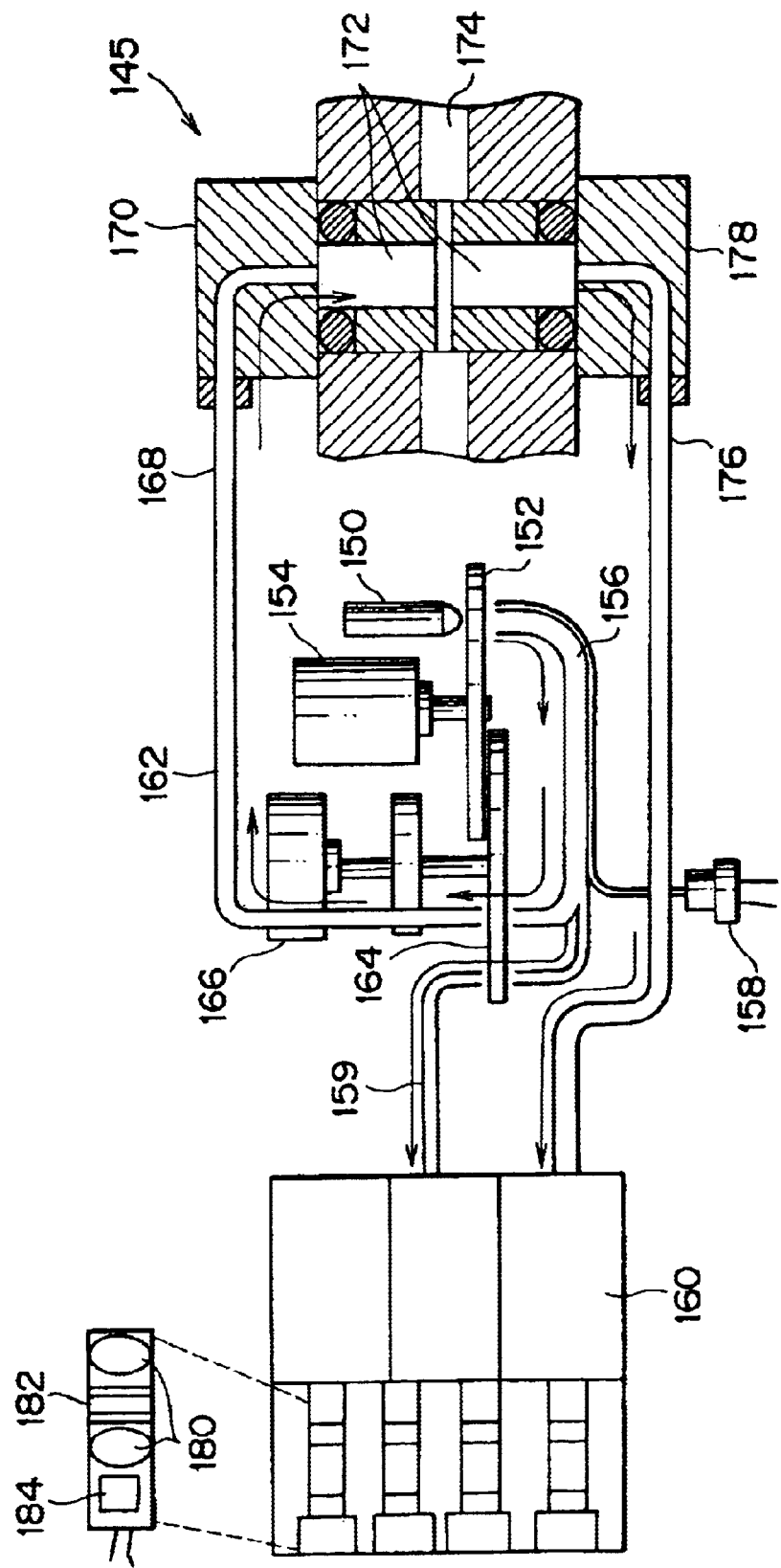
FIG. 10 shows a diagrammatic view of a spectrometer module.

The spectrometer cell described above forms part of a spectrometer module, the basic structure of which is shown in FIG. 10. The spectrometer comprises a halogen lamp, broad spectrum light source 150 which passes light through a chopper wheel 152 (driven by a chopper motor 154) into an optical fibre bundle 156. Outputs are taken from the bundle 156 to provide input to a motor synchronisation photodiode 158, a source light input 159 to a light distributor 160 (forming part of the detector described in more detail below) and to a measure path 162 which provides input to the spectrometer cell 145. A calibration wheel 164 driven by a rotary solenoid switch 166 selects whether light passes into the source light input path 159, the measure path 162, or both. The input fibre bundle 168 connects to the input flange 170 of the cell and optically connects to the sapphire window 172. Light is transmitted from the window 172, across the flow path 174 through another sapphire window 172 and into an output fibre bundle 176 connected to the output flange 178. The output bundle also connects to the light distributor 160. The light distributor 160 distributes the light received from the source light input 159 and the output fibre bundle 176 to a number of different channels. For the purposes of this example, only four channels are shown but other numbers are practically useful. One particularly preferred example has eleven channels. Each channel comprises lens 180 and bandpass filter 182 arrangement feeding to a photodiode 184. The filters are chosen to select predetermined wavelengths of light for the channels in the range from visible to near infrared. Each channel provides an output signal relative to the wavelength in question.

The spectroscopy module has four modes, Sleep, Dark, Source, and Measure. When the module is in Sleep mode, the electric power is on but lamp 150 and chopper motor 154 are both off. The module detects nothing. When in Dark mode, lamp 150 and motor 154 are both on but the solenoid switch 166 blocks both source and measure paths 159, 162. No light is detected and the module measures background level. In Source mode, the solenoid switch 166 opens the source path 159 but the measure path 162 is still blocked. The light from lamp 159 can pass through the source path 159 and detected as a reference spectrum. When the module is in Measure mode, the solenoid switch 166 opens the measure path 162 and source path 159 is blocked. The light from the halogen lamp 159 goes into input fiber bundle 168 and passes through the fluid in the flowline 174 via the sapphire windows 172 and passes into the output fiber bundle 176 and from there to the distributor 160 and detected as the fluid spectrum data.

When used to determine GOR, it is necessary that the module has a channel that is sensitive to the methane peak in the measured spectrum. This peak occurs at 1671 nm with a shoulder at 1650 nm. Two approaches for detecting this peak are proposed. In the first a narrow band filter is used to detect only the 1671 nm peak. A suitable filter would have 1671 nm centre wavelength (CW) and 15 nm full width half maximum (FWHM). In the second approach, the channel detects both the peak and the shoulder. In this case, a 1657.5 nm CW and 35 nm FWHM filter can be used. The different filters give different responses for signal level and background level and so the choice of which is most appropriate will be made on a case by case basis. If desired, both wide and narrow band methane channels can be provided although this will be at the expense of the number of channels available for other wavelength measurements.

Figure 11:
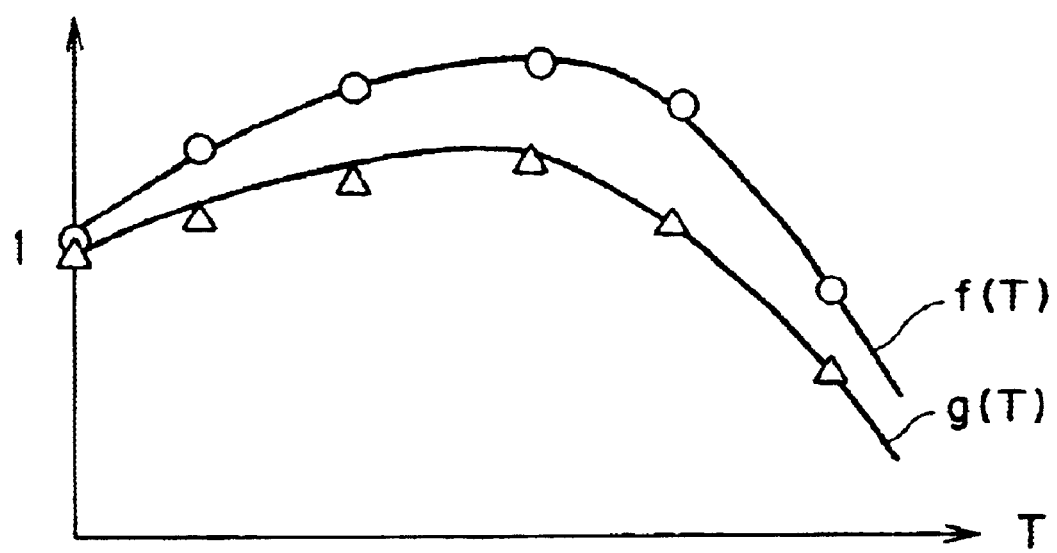
FIG. 11 shows plot of temperature compensation data.

As the GOR measurement is absolute measurement, the measurement accuracy of the spectrum is very important. In order to keep the measurement accuracy over the temperature range from 25 to 175° C., a temperature compensation system is introduced. First measure mode data ($M_{cal}(T_i)/M_{cal}(T_0)$, in FIG. 11) and source mode data ($S_{cal}(T_i)/S_{cal}(T_0)$, ▲ in FIG. 11) are acquired at several temperature from 25° C. to 175° C. All data are normalised relative to the room temperature (25° C.) data.

Fitting curves for measure data (f(T)) and source data (g(T)) as a function of temperature are created using least square method for these data.

Figure 12:
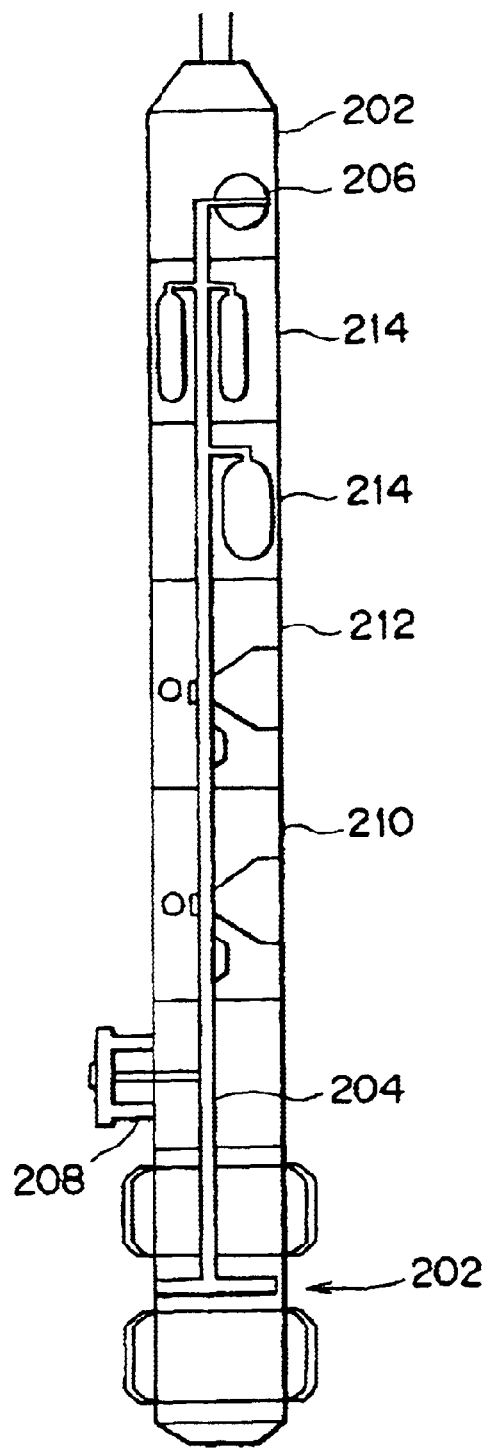
FIG. 12 shows an embodiment of a tool according to an aspect of the invention with two spectroscopy modules.

Actual measurement data from the spectrometer module in use are compensated with $$M(T)/M(T_0) \rightarrow \frac{M(T)/M(T_0)}{f(T)}$$

$$S(T)/S(T_0) \rightarrow \frac{S(T)/S(T_0)}{g(T)}$$

$$\Downarrow$$

$$OD = -\log\frac{M(T) \cdot S(T_0) \cdot g(T)}{M(T_0) \cdot S(T) \cdot f(T)}$$

these fitting curves in the following manner:

As well as providing information about the composition of the fluids, the spectroscopy module can be used to give information about the flow rate of fluids in the tool. FIG. 12 shows one tool configuration which has two spectroscopy modules connected in series with a common flow line. By correlating the outputs of the two modules over time, the flow rate of fluid in the flow line can be determined and the appropriate sampling time derived. The tool configuration shown in FIG. 12 comprises a tool body 200 having a packer module 202 at its lower end and a flow line 204 running along its length to a pumpout module 206 located near its upper end. Above the packer module 202 is a probe module 208 which allows fluid communication between the formation and the flow line 204. Two spectroscopy modules 210, 212 are located above the probe module 208, connected in series to the flow line 204. Each spectroscopy module is substantially as described above in relation to FIG. 10. Above the spectroscopy modules 210, 212, is a series of sample chambers 214 connected to the flow line 204 for receiving samples of formation fluid. In the tool of FIG. 12, this time can be the time at which fluid is admitted to on or other of the sample chambers and can be selected to ensure minimum contamination by drilling fluid or filtrate.

The various embodiments of the apparatus described above can be used to make a number of measurements which can be used to provide information about the formation fluids. For example, OD-based measurements distinguishing between crudes and filtrate determination (as described in U.S. Pat. No. 5,266,800, incorporated herein by reference), or oil/water phase analysis (as described in U.S. Pat. No. 5,331,156, incorporated herein by reference) can be performed with this apparatus.

Figure 13:
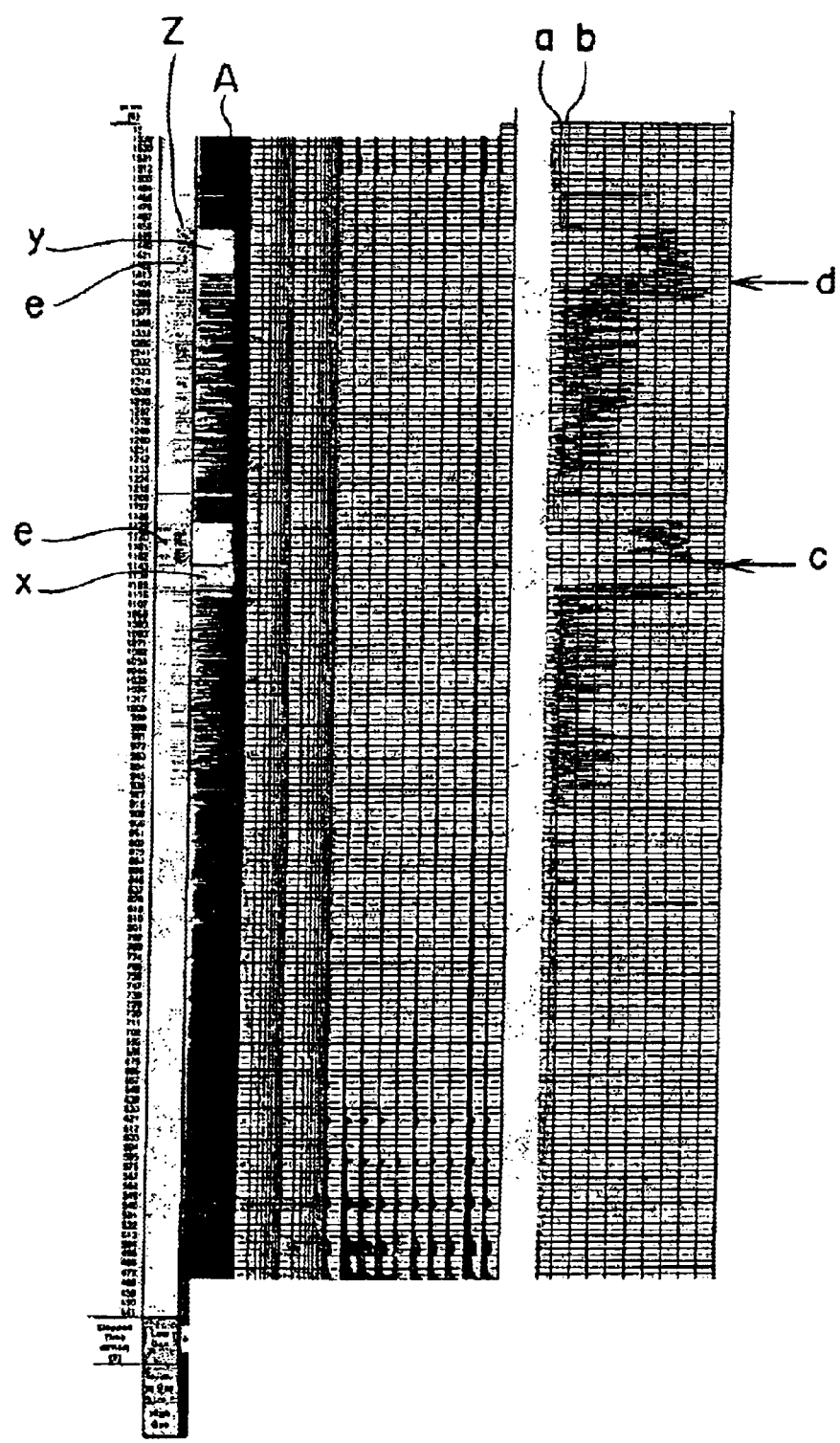
FIG. 13 shows a section of log against time for a sample including gas.

Gas detection can be performed in the manner described in U.S. Pat. No. 5,201,220 (incorporated herein by reference). However, an alternative method is possible using the methane detection channel output. Since this channel measures the methane absorption spectrum, measurement of GOR (see below for further details) can be used for the Gas Detector. FIG. 13 shows the log example in which gas is present in oil-based mud (OBM). The log shows the oil/water fraction track A shows the presence of gas in region x and y which is confirmed by the gas detector track Z which is based on the method described in the '220 patent referenced above. The GOR values are shown as tracks a and b (corresponding to the narrow and wide band filters for the methane channel described above), the increase in GOR at points c and d corresponding to the white area change in oil/water fraction track at points x and y. GOR values show very good agreement with white part of the oil/water fraction track and with the gas detector track e. Since the gas detector detects gas near the detector window, small gas bubbles inside the flowline might not be detected and when the window surface is covered the mud or dark oil, the gas detector often does not work. In both cases, GOR measurements can be made and consequently gas detected. Since the gas being detected is methane, and the apparatus has at least one channel responsive to the methane absorption peak, it is possible to use the output of this channel directly as a gas detection indicator. It is not necessary to determine GOR first.

The method of determining GOR is developed on the basis of experimental NIR measurements on prepared binary mixtures of methane and heptane, and live crudes obtained in the field. NIR spectra were acquired with a Cary 5 UV-Visible-NIR Spectrometer. The spectrometer optical beam is interfaced with a high pressure, high temperature (HPHT) spectroscopy cell fitted with sapphire windows substantially as described above. The internal pathlength in the cell is 2 mm. The attenuation incurred by use of the interface optics and cell was approximately 1.5 OD units. The rear beam attenuator was employed in the Cary at a level of OD=~1.2 extending the limit of measurable OD.

FIG. 14 shows a schematic of the apparatus used to obtain the data. The flowline of the measurement cell 300 is connected via high pressure transfer lines 302 to the conventional sample bottle (CSB). The CSB which can hold 20,000 psi under controlled conditions, has an internal sample volume 304 separated from the hydraulic fluid volume 306 by a floating piston 308. The CSB's contain an internal agitation ring (not shown) allowing for effective sample mixing when the bottle is rocked. The far end of the sample flowline 310 is fitted with a valve 312 allowing for fluid transfer with bleeding under high pressure conditions to purge any sample flashed during transfer due to the cell dead volume. The CSB hydraulic side is connected to a high pressure pump 315 and a pressure gauge 316 to control the pressure. The sample cell 300 is situated inside an oven 318 for temperature control.

Mixtures of methane and heptane are and transferred to a CSB. The samples are recombined into a single phase by pressurizing ~2000 psi above the bubble point with agitation. After recombination, the sample is transferred to the measurement cell at high pressure. Approximately 10 times the dead volume is bled off to prevent flashed sample discrepancies. Multiple runs can be performed which verify consistency. The gas-liquid ratio of the sample was evaluated to check sample composition.

Live crude oils are obtained and transferred to CSB's. The samples are then transferred to the HPHT cell at bottom hole temperature and pressure. After heating and pressurizing the sample, it is agitated for a period of 15 to 30 minutes until the pressure is unchanged upon further agitation. Heating prevents waxes from phase separating, while pressure is required to avoid any separate gas phase. If the sample in the CSB becomes two phase during transfer, then sample transfer results in a nonrepresentative sample being removed from the sample bottle, invalidating both the removed and remaining samples. GOR of these live crude oils are determined by a commercial service in the conventional manner for confirmation.

For most crude oils, the primary gaseous component for gases at one atmosphere is methane. At high pressure, the gas phase (the lower density of the two fluid phases) can contain a much larger fraction of heavier hydrocarbons than gases at one atmosphere. Except for unusual gas phase which contains very high concentrations of $H_2S$ (or $CO_2$), there is a monotonic relationship between dissolved methane and GOR. At the lower GOR's listed the relationship is linear. The present method attempts to provide GOR from methane (or from the alkane fraction), but not from $H_2S$ or $CO_2$. By measuring the dissolved methane mass fraction of crude oil, it is possible to determine the hydrocarbon component of GOR. Since this component normally dominates GOR, then for normal circumstances, GOR is determined.

The basic analysis of GOR is based on equations relating the GOR of prepared binary mixtures of n-heptane (representing oil) and methane to the NIR spectra. As crude oils can be related to these binary mixtures, the resulting equations can be used for crude oil GOR determination as well.

The method of determining GOR employs the concept of placing an NIR channel on the methane peak at ~1670 nm and a second NIR channel at ~1725 nm (—$CH_2$— and —$CH_3$). A response matrix $\hat{B}$ is formed with the first column the response of methane in these two channels and the second column the oil response in these two channels.

The signal response in the two NIR channels ($\vec{S}$ vector) and the mass fraction vector of a binary methane-heptane mixture ($\vec{m}$ vector) giving $\vec{S}$ as the signal vector are related to $\hat{B}$ according to equation 1:

$$\vec{S} = \hat{B}\vec{m} \qquad 1$$

Solving equation 1 using Cramer's rule:

$$m1 = \frac{D_1}{D} \text{ and} \qquad 2$$

$$m2 = \frac{D_2}{D} \qquad 3$$

where D is the determinant of $\hat{B}$, $D_1$ is the determinant obtain from the matrix with $\vec{S}$ replacing the first column of $\hat{B}$, and $D_2$ is obtained by replacing (only) the second column of $\hat{B}$ in the usual manner.

For a binary methane-n-heptane mixture, mass fraction $\vec{m}$ can be used to obtain the corresponding GOR. It is presumed that the gas phase contains all of the methane (m1) plus heptane vapor at its equilibrium vapor pressure.

The GOR of the mixture is given by:

$$GOR = 5945 \frac{m1}{m2 - 0.257m1} (scf/bbl) \qquad 4$$

When the mass fraction of heptane drops to a value where it is just able to provide its equilibrium vapor pressure, but yields no liquid, the GOR is infinite. Eq. 4 does not apply to smaller heptane mass fractions than this.

Using spectrometer data obtained with the experimental apparatus described above, the $\hat{B}$ matrix elements are generated by obtaining the slopes of the integrated and average spectrometer OD values (<OD>) curves over specified wavelength windows for methane and for heptane. FIGS. 15 and 16 show the resulting data used to generate the $\hat{B}$ matrix which corresponds to spectrometer data for methane and heptane. This $\hat{B}$ matrix is dependent on specifics of the optical system so must be determined for each new optical spectrometer.

For the integration <1640–1675>, the $\hat{B}$ matrix is obtained from values listed FIGS. 15 and 16.

$$\hat{B} = \begin{pmatrix} 1.657 & 0.099 \\ 0.882 & 1.614 \end{pmatrix}$$

For the integration <1660–1675>, the $\hat{B}$ matrix is obtained from values listed FIGS. 15 and 16.

$$\hat{B} = \begin{pmatrix} 1.838 & 0.123 \\ 0.882 & 1.614 \end{pmatrix}$$

Figure 17:
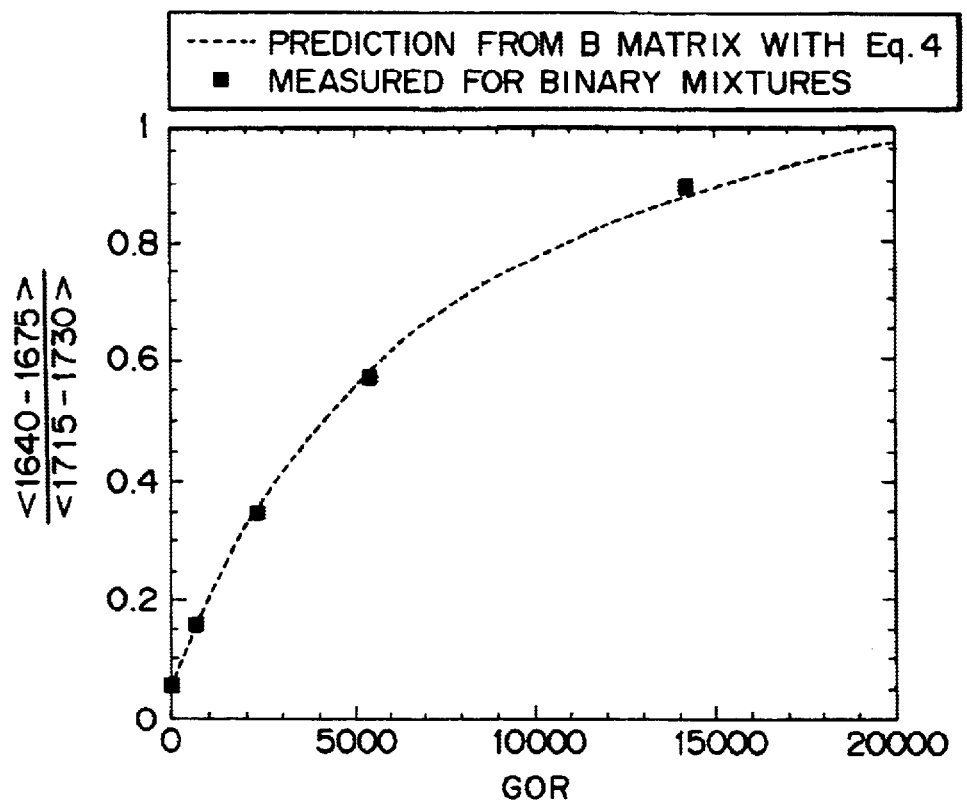
FIG. 17 shows values of GOR predicted according to an aspect of the invention vs. actual values measured for binary mixtures.

Using Eq. 4, it is possible to calculate the theoretical dependence of the NIR signal on GOR. This is plotted in FIG. 17 for the integration <1640–1675> along with the values measured for the binary mixtures with excellent agreement over a broad range of GOR's in spite of no adjustable parameters. The values shown in the $\hat{B}$ matrices discussed above are dependent upon the particular optical system used and can be individually adjusted to accommodate an improved understanding of gas-oil mixtures if required.

Figure 18:
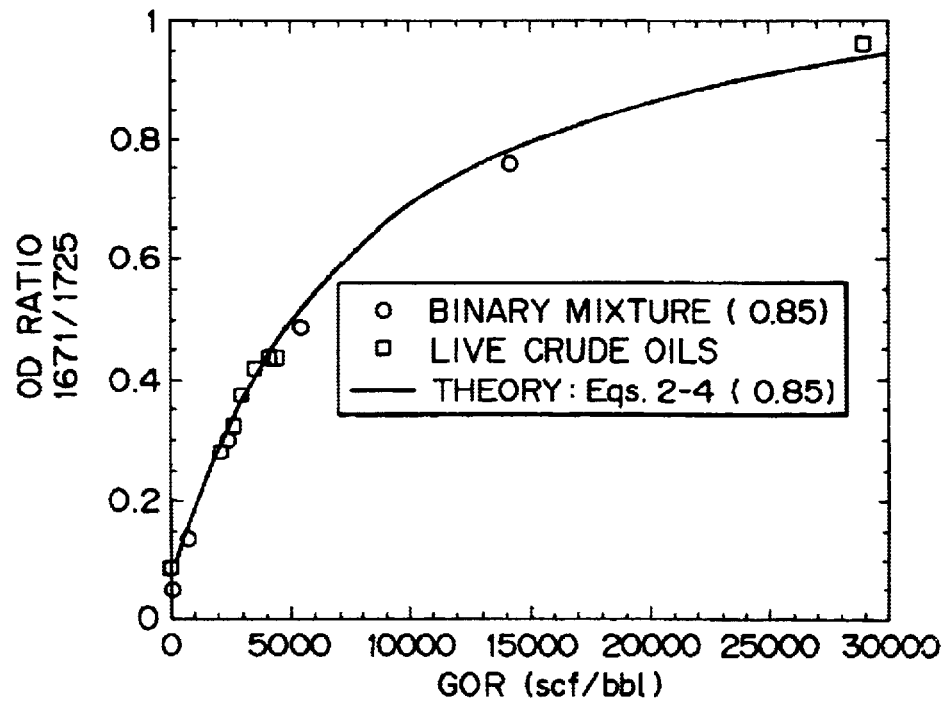
FIG. 18 shows the corresponding plot with live crude samples and theoretical an binary mixture figures adjusted by a constant.

FIG. 18 shows the ratio of peak areas for a series of live crude oils and for four binary mixtures. The OD ratio for the binary mixtures was reduced by a factor of 0.85 (described below). The line in FIG. 18 corresponds to the predictions of Eq. 4 (also reduced in the ordinate by a factor of 0.85). Monotonic behavior is seen for this diverse collection of live crude oils over a broad range of GOR's. Similarly, the binary mixtures also exhibit the same monotonic behavior, again over a very large range of GOR. The trends for both sets of samples live crude oils and binary mixtures are predicted by Eq. 4, but for the live crude oils the modification by a factor of 0.85 must be included. Thus, with minor modification, Eq. 4 can be used to analyze the spectrum of a single phase live crude oil to predict its GOR.

By far, the biggest source of the nonunity term (0.85) is the difference in gas composition between the binary mixtures and the live crude oils. This factor of 0.85 accounts for the fact that the gas phase of live crude oils is frequently around 80 mole % methane while for the binary mixtures, the gas phase is about 96 mole % methane. The extent to which the gas fraction of a live crude oil deviates from 80 mole % is the error incurred predicting the GOR. In particular, if the gas phase of a live crude oil contains significant quantities of $H_2S$ or $CO_2$ then Eq. 4 would not provide the GOR of the crude oil, but rather, would provide the GOR due to hydrocarbons. Other techniques can be used to detect $H_2S$ and $CO_2$.

There can also be differences in the magnitude of the peak at 1725 nm for different dead oils. This peak which includes contributions from both the —$CH_2$— and —$CH_3$ groups can vary depending on components such as waxes or aromatics. However, detection and quantification of crude oil by analysis of this peak indicates that the variation is not so large, perhaps 10% and converts into an error bar on the corresponding GOR measurement, Error bars can be reduced for application where dead crude oil characteristics are known.

The apparatus described above can be used to determine the level of contamination in a sample of formation fluid in the flow line and so allow determination of an appropriate time for sampling to avoid interference from contaminants. Examples of methods for this determination can be found in U.S. Ser. No. 09/255,999, now U.S. Pat. No. 6,274,865 and U.S. Ser. No. 09/300,190, now U.S. Pat. No. 6,350,986 (incorporated herein by reference).

Figure 19:
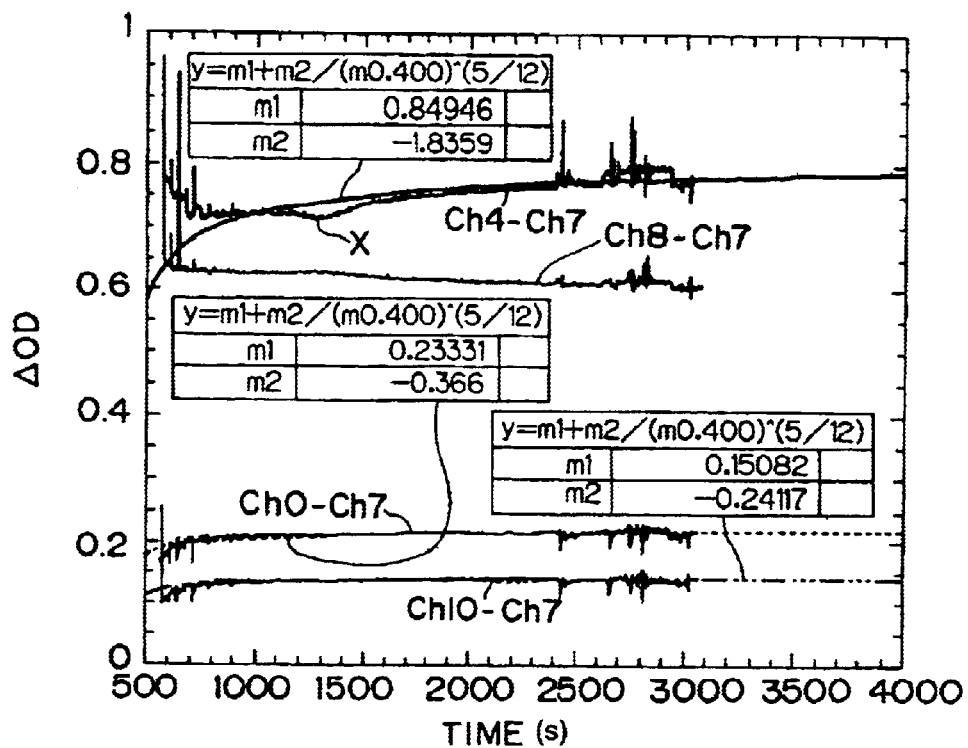
FIGS. 19 and 20 show plots of various spectrometer channels vs. time for scattering correction.
Figure 20:
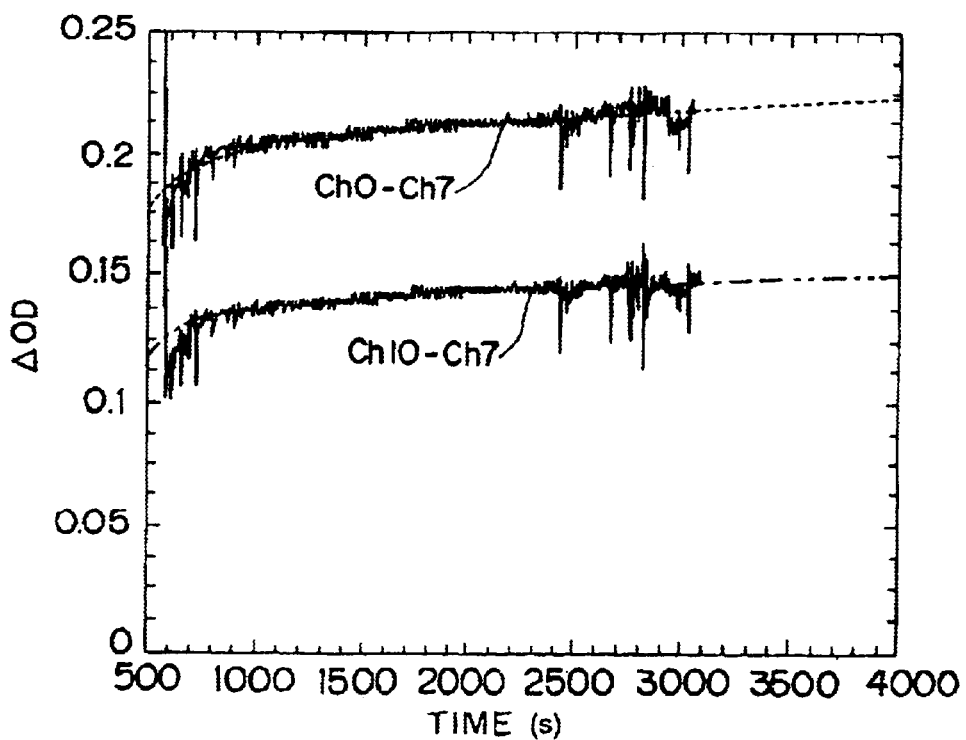

The methodology applied to the colour measurement for contamination determination can be applied to measurements made by the methane channel of the spectrometer. When making contamination determination based on colour, the output of the colour channel selected is corrected for wavelength independent scattering by subtracting the output of a reference channel. FIG. 19 shows plots of outputs from pairs of channels, together with fitting curves and the appropriate fitting curve formula FIG. 20 shows an expanded view of part of FIG. 19 for the GOR-dependent curves. In FIGS. 19 and 20, plots for colour (Channel 4–Channel 7) and reference (oil) (Channel 8–Channel 7) are shown. The colour output includes contribution from colour and scattering, whereas the reference shows only scattering. Thus correcting the colour output with the reference gives only colour together with some wavelength dependent scattering, the wavelength independent scattering being removed by subtraction. Since the colour and reference measurements are not the same wavelength, wavelength dependent scattering will not be removed by this method.

For colour measurements, it is necessary to use a reference channel that is hundreds of nm away to remove scattering in the manner described above. For example, in the case shown in FIG. 19, Ch4 and Ch7 are 530 nm apart (1070 nm and 1600 nm). The same general approach can be used for the methane channel (Ch0 in FIGS. 19 and 20). In this case, however, the reference channel (again Ch7) is close to the measurement channel (Ch0) giving a difference in wavelength of only 70 nm in the case of the present example (1670 nm–1600 nm). Consequently, this approach will also remove wavelength dependent scattering. Also, since wavelength dependent scattering cross section decreases with increasing wavelength, the use of the longer wavelength NIR methane channel (1670 nm) rather than the shorter wavelength colour channel (1070 nm) reduces wavelength dependent scattering. By applying this method, the wavelength dependent scattering seen at X in FIG. 19 in the colour channel is avoided and the level of contamination in the flow line can be estimated more reliably leading to better sample time determination.

As is described above in relation to FIG. 12 embodiments of the spectroscopy tool can also make flow rate measurements. Prior versions of the MDT tool calculate the flow rate in the flow line from the pump displacement and the number of pump strokes to give the pumped volume which is converted to flow rate by relation to time. However, this calculation is not always correct and a more accurate flow measurement is sometimes required. Where two spectroscopy modules are provided as shown in FIG. 12 flow rate can be calculated by cross correlating features in the same spectroscopy channel output in each module against time. From a knowledge of the flow line volume and the time of the peak in the correlation function, the flow rate can be determined. The accurate flow rate is required because it is necessary to calculate when to take a sample from the flow line since the sampling point is not the same as the measurement point.

What is claimed is:

1. A method of analyzing fluids from an underground formation using a spectrometer having a light source, a flow line including a measurement cell and a detector, the method comprising:

a) making spectroscopic measurements of fluids in the measurement cell at a measurement channel having a wavelength responsive to the presence of methane;

b) providing a reference channel;

c) correcting measurement channel with reference channel to remove scattering, wherein the correcting comprises subtracting the output of the reference channel from the measurement channel; and d) using the measurements to indicate the presence of gas in the flow line.

2. The method as claimed in claim 1, wherein the wavelength responsive to the presence of methane comprises approximately 1671 nm.

3. A method of analyzing fluids from an underground formation using a spectrometer having a light source, a flow line including more than one measurement cell and a detector, the method comprising:
   a) making spectroscopic measurements of fluids in at least one measurement cell at a measurement channel having a wavelength responsive to the presence of methane;
   b) providing a reference channel;
   c) correcting measurement channel with reference channel to remove scattering, wherein the correcting comprises subtracting the output of the reference channel from the measurement channel; and
   d) using the measurements to indicate the presence of contaminants in the fluid in the flow line.

4. The method as claimed in claim 3, wherein the wavelength responsive to the presence of methane comprises approximately 1671 nm.

5. A method of analyzing fluids from an underground formation using a spectrometer having a light source, a flow line including a measurement cell and a detector, the method comprising:
   a) making spectroscopic measurements of fluids in at least one measurement cell at a measurement channel having a wavelength responsive to the presence of methane;
   b) providing a reference channel;
   c) correcting measurement channel with reference channel to remove scattering; and
   d) using the measurements to indicate the presence of contaminants in the fluid in the flow line to determine a time to take a sample from the flow line for further analysis.

6. A method of analyzing fluids from an underground formation using a spectrometer having a light source, a flow line including a measurement cell and a detector, the method comprising:
   a) making spectroscopic measurements of fluids in the measurement cell at a measurement channel having a wavelength responsive to the presence of methane;
   b) providing a reference channel;
   c) correcting measurement channel with reference channel to remove scattering, wherein the correcting comprises subtracting the output of the reference channel from the measurement channel;
   d) making spectroscopic measurements of fluid in the measurement cell at a wavelength responsive to the presence of oil; and
   e) using the measurements to indicate the presence of contaminants in the fluid in the flow line.

7. The method as claimed in claim 6, wherein a wavelength responsive to the presence of oil comprises a wavelength responsive to the presence of alkanes.

8. The method as claimed in claim 6, wherein a wavelength responsive to the presence of oil comprises a wavelength responsive to the presence of $CH_2$.

9. The method as claimed in claim 6, wherein a wavelength responsive to the presence of oil comprises a wavelength responsive to the presence of $CH_3$.

10. The method as claimed in claim 6, wherein the wavelength responsive to the presence of methane comprises approximately 1671 nm.

11. The method as claimed in claim 6, wherein the wavelength responsive to the presence of oil comprises approximately 1725 nm.

12. A method for sampling fluids from a formation surrounding a borehole comprising:
   a) deploying a tool into a borehole, said tool comprising multiple optical analysis modules, each capable of making optical measurements sensitive to the present of gas, said modules connected by a flow line;
   b) establishing fluid communication between tool and formation, whereby formation fluids pass in said flow line;
   c) measuring in more than one optical analysis modules the formation fluid passing in flow line;
   d) cross-correlating an optical measurement of one of the multiple optical analysis modules with an optical measurement of at least one other of the multiple optical analysis modules, and
   e) determining the flow rate of fluid in flow line.

13. The method of claim 12, further comprising the step of:
   f) deriving a sampling time using the flow rate of fluid in said flow line.

14. The method of claim 13, wherein said cross-correlated optical measurement is sensitive to the presence of contaminants in fluid in the flow line.

15. The method of claim 14, further comprising the step of:
   g) sampling fluid in the flow line at a sampling time when the presence of contaminants is low.

16. The method of claim 12, wherein the step of cross-correlating an optical measurement comprises cross-correlating the same spectroscopy channel.

17. The method of claim 12, wherein the step of cross-correlating an optical measurement comprises cross-correlating a peak.

18. The method of claim 12, comprising two optical analysis modules, wherein said modules are spectroscopy modules.

19. The method of claim 12, wherein said cross-correlated optical measurement is sensitive to the presence of contaminants in fluid in the flow line.

20. A method for measuring flow rate in a flow line in a formation fluid sampling tool comprising:
   a) deploying sampling tool into a borehole, wherein sampling tool comprises two spectroscopy modules, each module capable of making measurements sensitive to the presence of gas in the formation fluid, said modules connected by a flow line;
   b) establishing fluid communication between sampling tool and the formation, whereby formation fluids pass in said flow line;
   c) measuring a channel peak using one spectroscopy module at a first time;
   d) measuring the same channel peak using the other spectroscopy module at a second time; and
   e) calculating the flow rate using the difference between said first and second times.

21. The method of claim 20, wherein said channel peak is measured at a wavelength responsive to the presence of contaminants in the flow line.

22. The method of claim 20, wherein said channel peak is measured at a wavelength responsive to the presence of alkanes in the flow line.

* * * * *